(12) United States Patent
Spenciner

(10) Patent No.: US 9,561,026 B2
(45) Date of Patent: Feb. 7, 2017

(54) SEGMENTED SUTURE ANCHOR

(71) Applicant: David B. Spenciner, North Attleboro, MA (US)

(72) Inventor: David B. Spenciner, North Attleboro, MA (US)

(73) Assignee: DePuy Mitek, LLC, Raynham, MA (US)

( * ) Notice: Subject to any disclaimer, the term of this patent is extended or adjusted under 35 U.S.C. 154(b) by 155 days.

(21) Appl. No.: 14/463,301

(22) Filed: Aug. 19, 2014

(65) Prior Publication Data
US 2016/0051245 A1 Feb. 25, 2016

(51) Int. Cl.
*A61B 17/04* (2006.01)
*A61B 17/16* (2006.01)

(52) U.S. Cl.
CPC .......... *A61B 17/0401* (2013.01); *A61B 17/16* (2013.01); *A61B 2017/0403* (2013.01); *A61B 2017/0409* (2013.01); *A61B 2017/0412* (2013.01); *A61B 2017/0424* (2013.01); *A61B 2017/0438* (2013.01); *A61B 2017/0458* (2013.01)

(58) Field of Classification Search
CPC ................. A61B 17/0401; A61B 2017/044; A61B 2017/0414; A61B 2017/0438; A61B 2017/0445; A61B 2017/0464
See application file for complete search history.

(56) References Cited

U.S. PATENT DOCUMENTS

| | | | |
|---|---|---|---|
| 5,053,047 A | 10/1991 | Yoon | |
| 5,123,913 A | 6/1992 | Wilk et al. | |
| 5,269,783 A | 12/1993 | Sander | |
| 5,342,376 A | 8/1994 | Ruff | |
| 5,425,747 A | 6/1995 | Brotz | |
| 5,584,859 A | 12/1996 | Brotz | |
| 5,931,855 A | 8/1999 | Buncke | |
| 5,968,047 A | 10/1999 | Reed | |
| 6,264,675 B1 | 7/2001 | Brotz | |
| 7,494,496 B2 | 2/2009 | Swain et al. | |
| 7,582,105 B2 | 9/2009 | Kolster | |
| 7,658,750 B2 | 2/2010 | Li | |
| 8,840,643 B2 * | 9/2014 | Dreyfuss | A61B 17/0401 606/232 |
| 2002/0022861 A1 | 2/2002 | Jacobs et al. | |
| 2008/0086138 A1 * | 4/2008 | Stone | A61B 17/0401 606/265 |
| 2009/0149883 A1 * | 6/2009 | Brunsvold | A61B 17/0401 606/232 |
| 2010/0076497 A1 | 3/2010 | Zwirkoski | |
| 2010/0121376 A1 | 5/2010 | Li | |

(Continued)

*Primary Examiner* — Tuan V Nguyen

(57) ABSTRACT

Devices and methods for anchoring surgical sutures are provided. In general, a device as described includes an anchor assembly formed of a plurality of rigid anchor segments including a proximal segment and a distal anchor segment comprising a force transferring element, and at least one segment having at least one interdigitation element configured to create an engagement force between the at least one segment and a tissue. The device further includes a flexible member linking the plurality of anchor segments and configured to transition the anchor from a first, flexible configuration when the flexible member is in a relaxed state to a second, substantially rigid configuration when the flexible member is in a taut state.

20 Claims, 9 Drawing Sheets

(56) References Cited

U.S. PATENT DOCUMENTS

2010/0292732 A1* 11/2010 Hirotsuka .......... A61B 17/0401
606/232
2010/0298871 A1 11/2010 Ruff et al.
2011/0004243 A1* 1/2011 Dreyfuss ............ A61B 17/0401
606/232
2013/0268001 A1* 10/2013 Catanese, III ..... A61B 17/0401
606/232

* cited by examiner

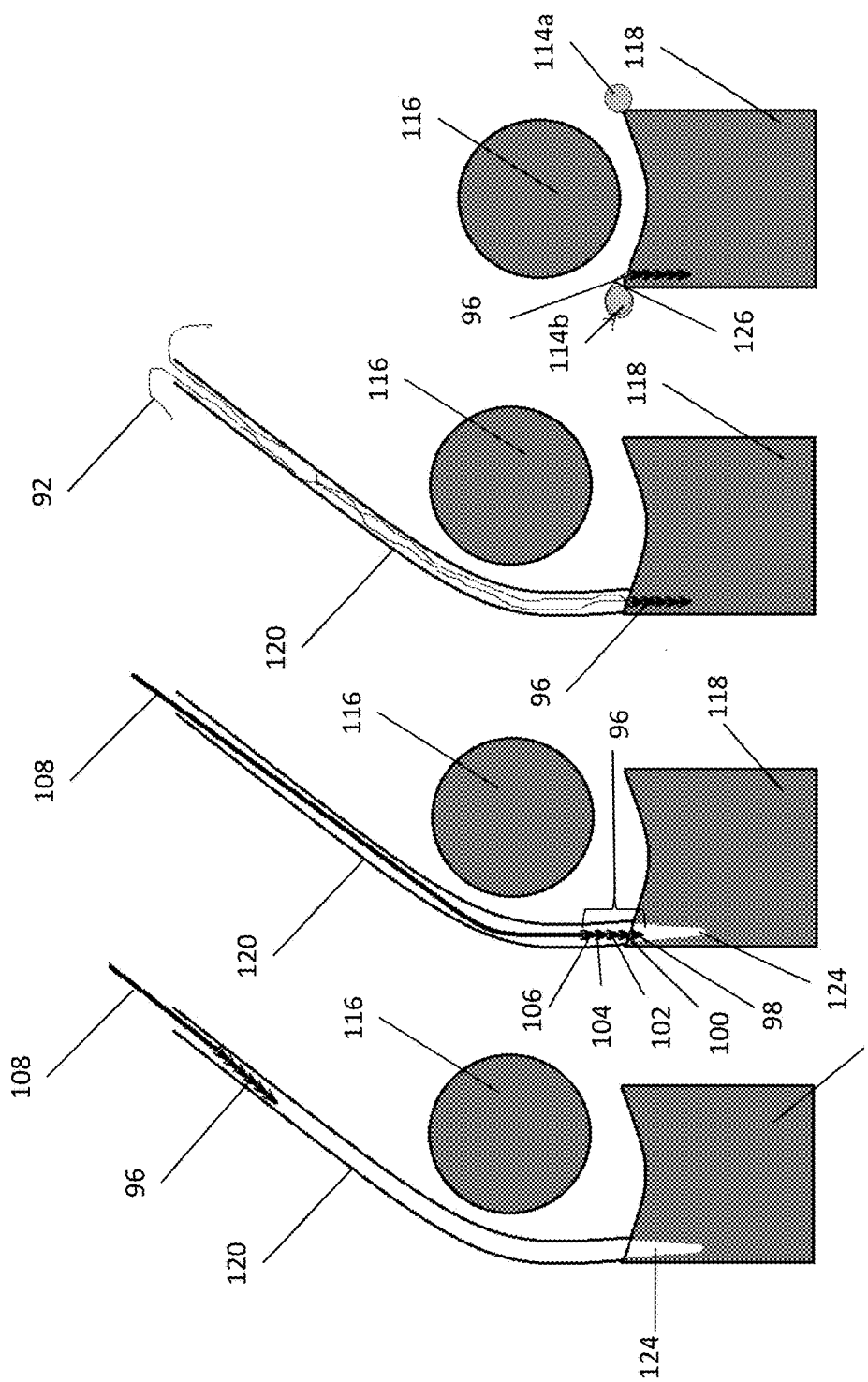

SEGMENTED SUTURE ANCHOR

FIELD

The present invention relates to suture anchor assemblies, and more particularly to suture anchor assemblies, surgical kits, and surgical repair methods.

BACKGROUND

Soft tissues, such as ligaments, tendons and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

A number of devices and methods have been developed to attach soft tissue to bone. These include screws, staples, cement, suture anchors, and sutures alone. Some of the more successful methods involve use of a suture anchor to attach a suture to the bone, and tying the suture in a manner that holds the tissue in close proximity to the bone.

The tissue may be attached to the bone during open surgery, or during closed (e.g., arthroscopic) surgical procedures. Closed surgical procedures are preferred since they are less invasive and are less likely to cause patient trauma. In a closed surgical procedure, the surgeon performs diagnostic and therapeutic procedures at the surgical site through small incisions, called portals, using instruments specially designed for this purpose. One problem encountered in the less invasive, closed surgical procedures is that the surgeon has significantly less room to perform the required manipulations at the surgical site. Thus, devices and methods are needed which will allow a surgeon to effectively and easily attach tissue to bone in the small spaces provided by less invasive surgical procedures.

Conventional methods for attaching soft tissue to bone typically require that the surgeon to attach the tissue to the bone using a suture. Anchoring a suture at the surgical site in closed surgical procedures, and even in open surgery, is difficult and time consuming due to inherent space constraints. Accordingly, there is a need for improved techniques for anchoring surgical sutures.

SUMMARY OF THE INVENTION

A surgical fastening device is provided that in some embodiments can comprise an anchor assembly formed of a plurality of rigid anchor segments including a proximal segment and a distal anchor segment comprising a force transferring element, and at least one segment having at least one interdigitation element configured to create an engagement force between the at least one segment and a tissue where the interdigitation element can comprise a bone engaging surface feature, and a flexible member linking the plurality of anchor segments and configured to transition the anchor assembly from a first, flexible configuration when the flexible member is in a relaxed state to a second, substantially rigid configuration when the flexible member is taut. Furthermore, the distal segment can have a substantially conical tip configured to assist an insertion of the plurality of anchor segments into the tissue and also have a smaller diameter than the proximal segment.

In some embodiments, the force transferring member can comprise one of an eyelet, a knot, and a cross pin and be operably coupled to the flexible element such that the application of a tensile force to the flexible member is effective to compress adjacent segments.

In some embodiments, each anchor segment can comprise a receiver element such as a lumen configured to receive the flexible member, where the lumen can extend through each segment such that the lumens of adjacent segments are oriented with respect to each other in one of a coaxial manner and a non-coaxial manner.

In some embodiments, each anchor segments can comprise a slot configured to receive the flexible member, where the slot extends through each segment such that the slot of adjacent segments are positioned with respect to each other in one of an aligned and mis-aligned manner.|[ML1]

In some embodiments, the flexible member can be a suture configured to connect each of the plurality of anchor segments, where each anchor segment can be of a substantially frustrum-like shape. Furthermore, the anchor assembly can include from about 4 to 7 such anchor segments configured to mate to one another. In some embodiments, the adjacent ends of adjacent segments can mate as a ball and socket and the anchor assembly can decrease in diameter from the proximal segment to the distal segment, where the proximal segment includes an interface element at the segment's proximal end configured to receive an insertion tool.

In another aspect of the present invention a surgical suture anchor assembly is provided to include a plurality of anchor segments configured to selectively interlock with each other, where each segment can include an internal lumen, a distal end and a proximal end, and a flexible member extending through the lumen of each of the plurality of anchor segments, the flexible member being operatively coupled to a force transferring element on a terminal segment and being configured to transform the plurality of anchor segments from a flexible assembly to a substantially rigid body when tension is applied thereto, where the substantially rigid body can assume a substantially linear or non-linear configuration.

In another aspect, a surgical method is provided that in some embodiments comprises delivering a suture anchor assembly formed of a plurality of substantially rigid segments to a cavity formed in a bone, where the suture assembly has a delivery configuration in which the suture assembly is flexible and able to assume a non-linear orientation. The method further includes anchoring the suture anchor assembly in a delivered configuration within the cavity such that the suture anchor assembly assumes a substantially rigid configuration by tensioning a flexible member extending through the assembly, passing a suture attached to the suture anchor assembly through a detached soft tissue, and tensioning the suture to re-approximate detached soft tissue. The method can also include passing the suture anchor assembly through a curved pathway. In some embodiments, the suture anchor assembly forms one of a linear orientation and a non-linear orientation in the delivered configuration.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 9A to 9D are schematic illustrations of steps of reattaching a soft tissue in accordance with some embodiments.

DETAILED DESCRIPTION

Figure 1:
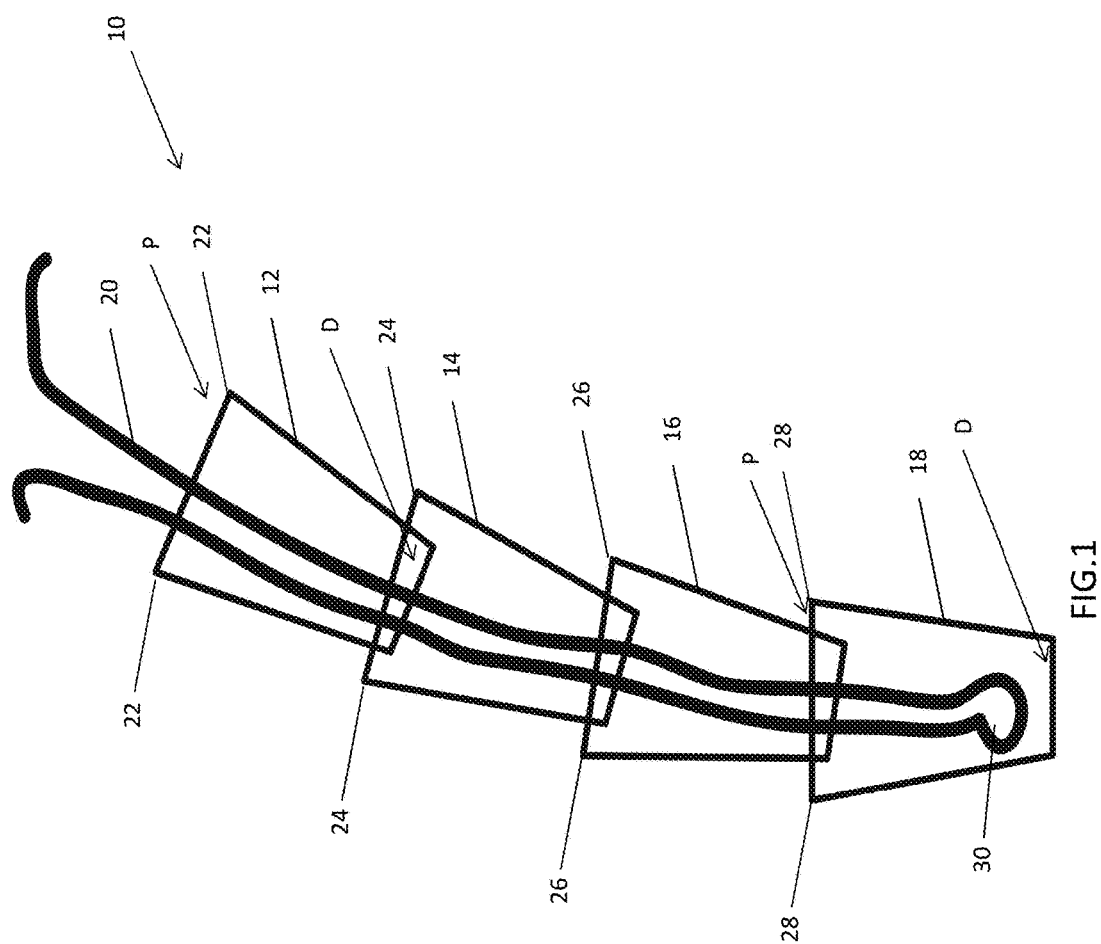
FIG. 1 is a schematic illustration of an anchor assembly in a flexible configuration in accordance with some embodiments.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Described herein are suture anchor assemblies, surgical kits, and methods of deploying suture anchor assemblies. In general, a suture anchor assembly disclosed herein is useful for repairing tissue damage, and particularly for attaching soft tissue to a bone structure. This anchor assembly is capable of assuming a delivery configuration, where the assembly is flexible, and a rigid configuration, where the assembly forms a substantially rigid body upon deployment in tissue. The anchor assembly includes a plurality of separate anchor segments linked together by a flexible member, where the flexible member passes through and/or is connected to substantially all of the segments. The flexible member can be further coupled to a force transferring element incorporated into one of the anchor segments (e.g., a most distal segment), such that when it is tensioned or pulled, the flexible member can import a force that compresses the assembly and pulls the adjacent anchor segments into proximity to one another. As a result of this action the assembly is compressed, transforming the anchor assembly from the flexible delivery configuration to the rigid configuration. Once in the rigid configuration, the anchor segments lock into one another and form a substantially rigid construct that acts in a manner substantially similar to a rigid, one-piece suture anchor.

The anchor assembly described herein is particularly advantageous in that the assembly can be inserted into a patient's body and into tissue cavities while in the flexible configuration, thereby allowing a surgeon to insert the device through curved pathways to bypass tissue structures when placing the anchor assembly at an optimal surgical location. Once the anchor assembly is properly positioned, the surgeon can transform the anchor assembly into its substantially rigid configuration. When the assembly is deployed in a patient, such as in a bone cavity, the geometry of the separate, individual anchor segments, including an interdigitation element formed on the segments, engages the bone, such as through a friction fit or positive engagement in bone, to provide sufficient force to secure the anchor assembly within the tissue cavity.

FIG. 1 illustrates a suture anchor assembly 10 assuming a flexible configuration, e.g., during delivery, in accordance with embodiments of the subject matter described herein. The suture anchor assembly 10 can include a plurality of separate anchor segments 12, 14, 16, 18 linked together by a flexible member, e.g., a suture 20, where each segment 12, 14, 16, 18 can have a proximal end P and a distal end D. While FIGS. 1-2 and 4-6 illustrate anchor assemblies with four anchor segments, it is understood that fewer or more segments can be utilized for anchoring surgical sutures. For example, anywhere from 2 to 7 or more segments can be used, depending upon the requirements of a given application.

The individual suture anchor segments can have virtually any shape that enables one anchor segment to mate with an adjacent segment. For purposes of illustration, the anchor segments are shown as being substantially frustrum shaped. However, a person skilled in the art will appreciate that other shapes can be used as well. Examples of other suitable shapes include conical, spherical, cuboid, pyramidal, or any other generally known geometrical configurations that are commonly known in the art.

Further, the geometry of the individual segments can be designed to enable mating of adjacent anchor segments as well as easy insertion into engagement with a cavity, such as a bone cavity. In the embodiment illustrated in FIGS. 1 and 2, for example, the distal ends D of each anchor segment can have a smaller diameter than the proximal end P of the same segment. Such a structure is one way to facilitate mating of the proximal end of one anchor segment with the distal end of an adjacent anchor segment. A variety of mating configurations can be used as well, as will be appreciated by a person skilled in the art. In one example, one end (e.g., a distal end) of a segment can be a male member that mates within a female receptacle of one end (e.g., a proximal end) of an adjacent segment. One example of such a male-female mating configuration is a ball and socket in which the proximal and distal ends of adjacent anchor segments can mate to one another as a ball and socket. Other mating configurations can include a round cavity, a hinge joint, pin-and-cup joint, conically tapered joint, or any other generally known means of male-female mating that is commonly known in the art. A person skilled in the art will appreciate that the relative dimensions of the male and female members should be such as to join the adjacent segments.

Figure 3A:
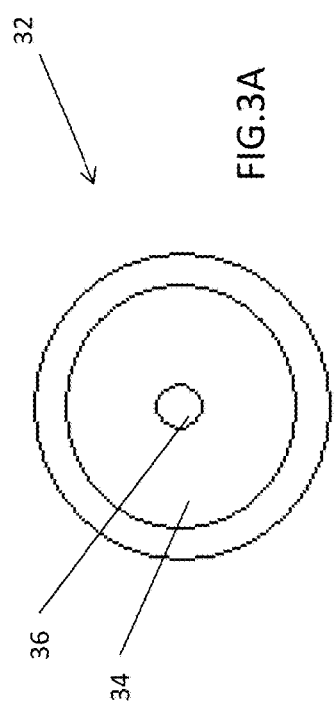
FIG. 3A is a proximal end view of an anchor segment in accordance with some embodiments.
Figure 3B:
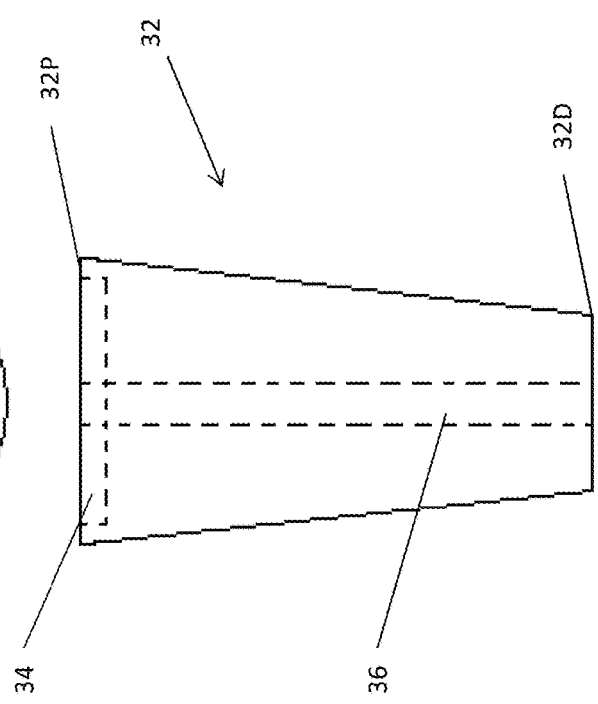
FIG. 3B is a side view of an anchor segment in accordance with some embodiments.

As depicted in FIGS. 3A and 3B, an exemplary anchor segment 32 can be substantially frustrum-shaped with a distal end 32D and a proximal end 32P, where the proximal end 32P is larger in size than the distal end 32D. The proximal end 32P can further include an interface element 34 configured to interface with a distal end of an adjacent anchor segment. The interface element can be one of a round cavity, a ball-and-socket, hinge joint, pin-and-cup joint, or any other generally known means of interaction that is commonly used in the art. Similarly, individual anchor segments can have a variety of shapes for facilitating an interdigitation between the anchor assembly and the bone.

Figure 2:
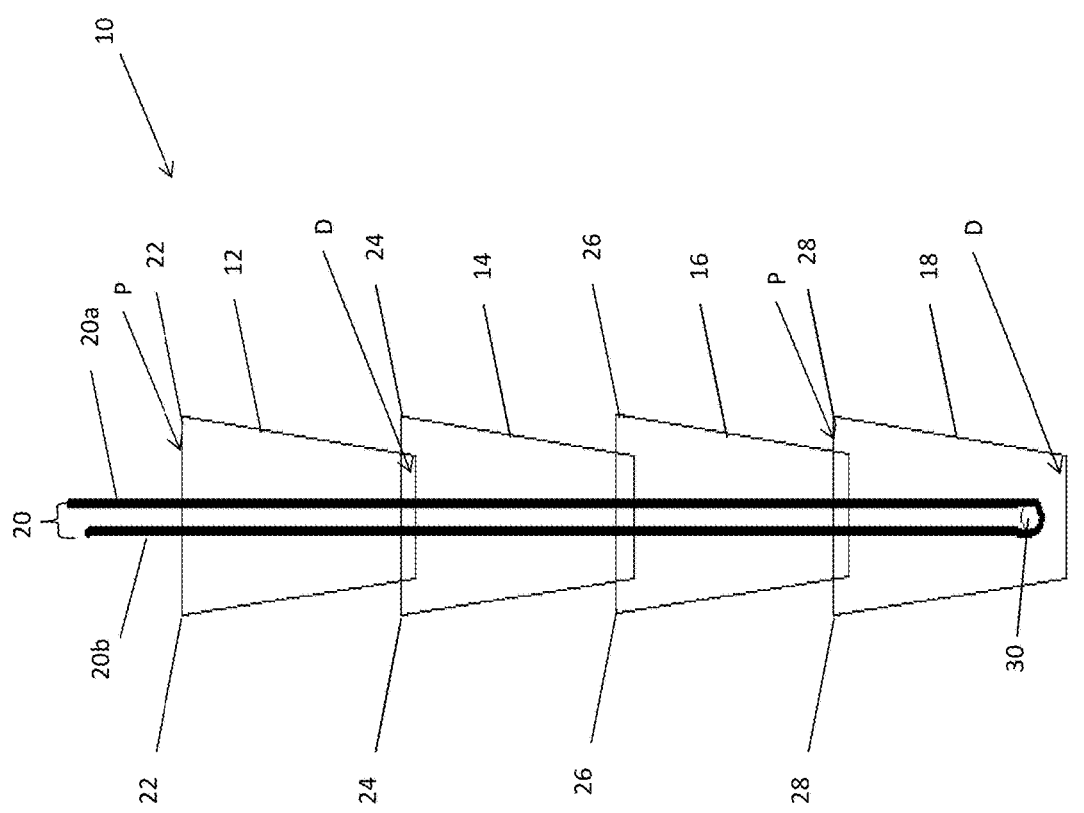
FIG. 2 is a schematic illustration of an anchor assembly in a rigid configuration in accordance with some embodiments.

FIGS. 3A and 3B further illustrate an exemplary anchor segment 32, which can be used with the anchor assemblies disclosed herein. As shown, each anchor segment can have a structure for receiving one or more flexible members such as a suture. In one embodiment, the anchor segments can include a receiver element 36, such as a lumen or a cannulation configured to receive the suture 20. With reference to FIGS. 1 and 2, for example, a suture 20 connects the individual anchor segments of the anchor assembly by passing through the lumen in each anchor segment that forms the anchor assembly. In arranging the suture to pass through the lumen a person skilled in the art will understand that one or more limbs of the suture can pass through each anchor segment, and further that more than one suture can be used. In some embodiments, individual anchor segments can have a receiver element in the form of a slot, where the slot can extend through each segment and be structured to receive a flexible member. When the anchor segments are stacked together, the slots can be purposely mis-aligned to prevent the segments from being disengaged from adjacent segments.

A person skilled in the art will also appreciate that the geometry of the anchor segments can be designed to promote fixation within a bone cavity. For example, each anchor segment can include features for creating and/or enhancing an engagement force between the segment and a tissue. As illustrated in FIGS. 1 and 2, for example, ridges 22, 24, 26, 28 can be formed on the proximal ends P of each anchor segment to create an interdigitation force between the segments 12, 14, 16, 18 and the surfaces that define inside a bone cavity. For example, when a tensile force is applied to the suture 20, the anchor assembly assumes a rigid configuration and as it is forced into the bone cavity its ridges 22, 24, 26, 28 can engage the inner wall of the bone cavity to create a sufficient engagement force to prevent the anchor assembly 10 from being pulled out of the bone cavity. A person skilled in the art will appreciate that other segment shapes (e.g., conical, spherical, cuboid, pyramidal) can also be conveniently utilized for securing a surgical anchor assembly as described herein, and that additional surface features, such a protrusions, can be formed on the anchor segments to enhance fixation within bone. In addition, in some embodiments the anchor segments 12, 14, 16, 18 can include thread structures (not shown) configured to facilitate a twist-in style of insertion into the bone cavity. For example, threads can be formed on the out-facing surface of the anchor segments, and as such, the anchor assembly 10 can be rotated into a bone cavity.

As explained above, a force can be applied or transferred onto the anchor segments 12, 14, 16, 18 by pulling on the suture 20, which is coupled to a force transferring element 30, shown in FIGS. 1 and 2 to be associated with the distal most anchor segment 18. A person skilled in the art will appreciate that the force transferring element can be any structure to which the suture 20 can attach or contact to transfer a tensile force on the suture to a force that pulls towards one another the adjacent segments of the suture anchor assembly 10. In some embodiments, the force transferring element 30 can be one of an eyelet, a knot, and a cross pin incorporated into one or more of the anchor segments. In one embodiment the force transferring element is formed in a distal most segment 18 of the anchor assembly so that the limbs of the suture 20 can pass around the transferring element 30. As explained in further detail below, when a pulling force is applied onto the suture 20, the suture 20 can apply a compressional force to the anchor assembly 10 to cause all the anchor segments 12, 14, 16, 18 to move toward one another to lock into an adjacent segment 12, 14, 16, 18 and transition from the flexible configuration (FIG. 1) to the substantially rigid configuration (FIG. 2).

In the delivery configuration, such as when the suture 20 is relatively relaxed, the suture is somewhat loose and flexible inside the anchor segments 12, 14, 16, 18, and the anchor segments 12, 14, 16, 18 can assume the flexible configuration in which the segments 12, 14, 16, 18 rotate along a non-longitudinal axis with respect to each other, as illustrated in FIG. 1. The degree of flexibility of the assembly can be such that the anchor segments 12, 14, 16, 18 can become partly or wholly disengaged from adjacent segments, and the anchor assembly 10 as a whole can be curved, forming a non-linear shape and thus allowing a surgeon to insert the anchor assembly 10 through a curved pathway. For example, for shoulder and hip surgeries to repair soft tissues, clear access to the optimal bone site can be difficult, but a flexible and bendable suture anchor assembly can be inserted through a curved bone hole or cavity using a flexible inserter (not shown in FIG. 1), thereby allowing the surgeon to pass around anatomical structures to deploy the anchor assembly in an optimal bone site.

Once the anchor assembly is inserted in a flexible delivery configuration, tensile forces can be applied to transform the anchor assembly into a rigid configuration, to assist anchoring a surgical suture. FIG. 2 illustrates the anchor assembly 10 in the rigid configuration in which individual anchor segments 12, 14, 16, 18 are locked into one another and form a rigid construct after a tensioning force is applied to at least one limb 20a, 20b of the suture 20. The suture 20 can be configured to engage a portion of distal anchor segment 18, such as to wrap around force transferring element 30. When the suture 20 is made taut, the suture 20 acts on the force transferring element 30 to transfer the tensioning force into a force that pulls together the anchor segments 12, 14, 16, 18. The anchor segments will thus engage or lock onto each other and form a substantially rigid construct, which will engage the walls of a bone cavity in an interference fit. Furthermore, depending on the shape of the bone hole, the segments may or may not return to a completely linear arrangement.

Figure 4:
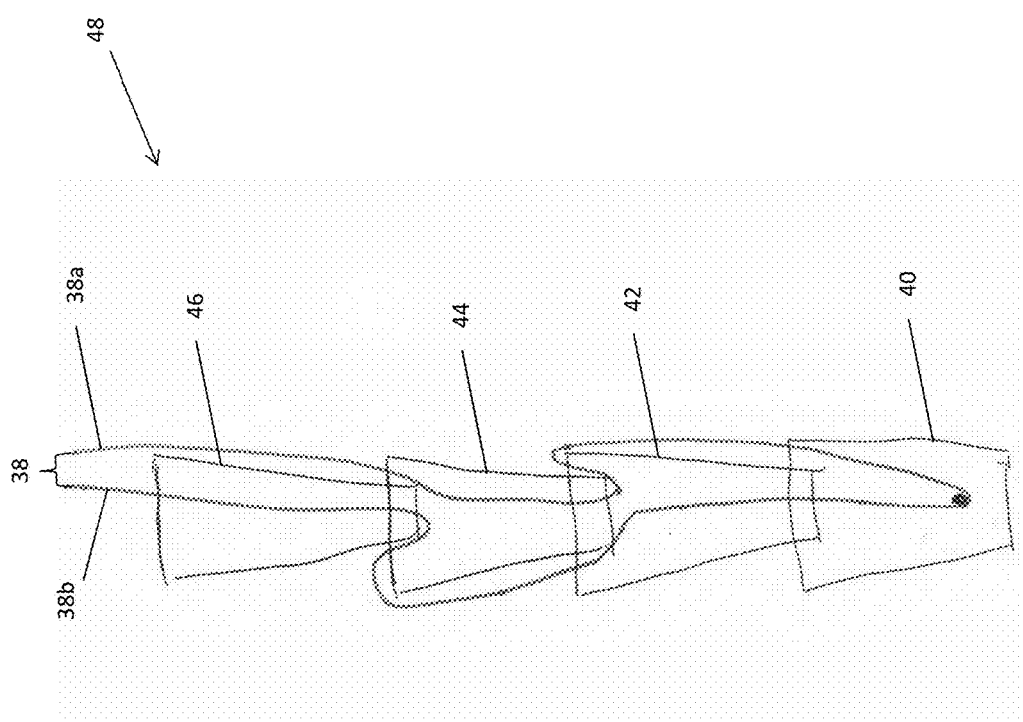
FIG. 4 is a schematic illustration of an anchor assembly with a partially exposed flexible member in accordance with some embodiments.

The individual anchor segments can be joined together or connected in a variety of ways to form an anchor assembly having a desired structure and/or set of properties. For example, instead of placing both limbs of a suture through every anchor segment, FIG. 4 illustrates an embodiment in which at least one limb of a suture 38 can be placed external to at least one anchor segment 40, 42, 44, 46. Such a configuration can help to increase an anchor assembly's 48 purchase within a bone cavity. FIG. 4 depicts that a left limb 38b of the suture 38 can be selectively placed outside the third anchor segment 44, while a right limb 38a can be selectively placed outside the second 42 and fourth 46 anchor segments. As such, when a pulling force is applied to both limbs 38a, 38b of the suture 38, the second 42 and fourth 46 segments will tend to shift to the left side due to a force exerted by the left suture limb 38b, while the third segment 44 will tend to shift to the right due to a force exerted by the right suture limb 38a. The resulting anchor assembly configuration 48, while still rigid, is no longer a substantially linear rigid construct as illustrated in FIG. 2, but instead has non-aligned anchor segments. As such, the anchor assembly can assume a larger overall geometrical profile inside the bone cavity compared to the profile described in FIG. 2. Accordingly, the interdigitation forces created between the anchor assembly and the wall that defines a bone cavity is also increased, thus providing additional resistance against anchor pull out. A person skilled in the art will appreciate that the exact order of which anchor segment 40, 42, 44, 46 is to be engaged by the limbs 38a, 38b of the suture can vary from configuration to configuration while the general principle illustrated here still applies.

Figure 5:
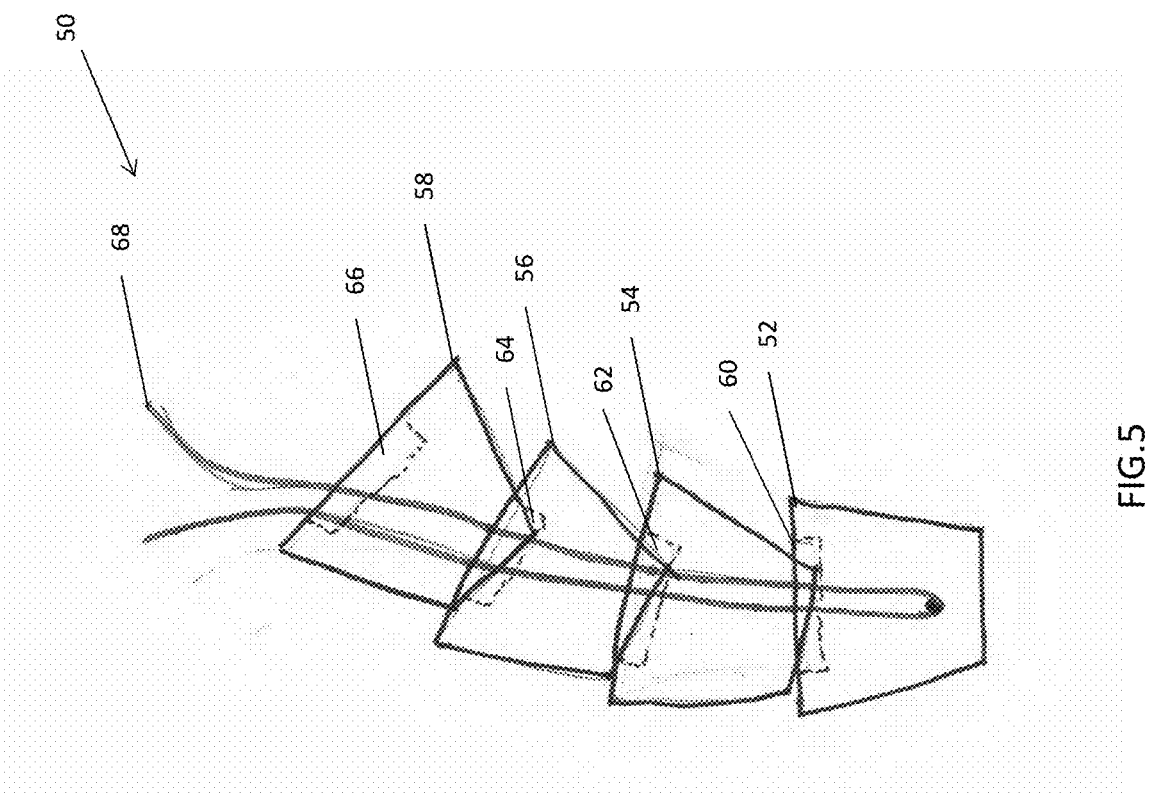
FIG. 5 is a schematic illustration of an anchor assembly with an off-axial cannulation in accordance with some embodiments.

Desired anchor assembly configurations can be created in other ways as well. FIG. 5, for example, illustrates an anchor 50 in which the anchor segments are not coaxial. As illustrated in FIG. 5, anchor segments 52, 54, 56, 58 can be tilted in respect to one another to bring the individual anchor segments 52, 54, 56, 58 off axis with respect to one another. For example, an anchor segment 54 can be purposely positioned out of the alignment with respect to an adjacent anchor segment's 52 receiving socket 60, and as such, the anchor segment 54 is tilted towards one direction (e.g., the right side). Similarly, third and fourth anchor segments 56, 58 of the anchor assembly 50 can also be purposely positioned out of the alignment in respect to an adjacent segment's sockets 62, 64 and tilted off axis. When the suture 68 is pulled taut by a surgeon, the anchor segments 52, 54, 56, 58 will rotate on each other and grasp onto the walls of a bone cavity in the manner of a thread structure, effectively increasing the anchor assembly's 50 engagement force within the bone cavity. This construction also enables the anchor assembly 50 to form a generally curved construct (e.g., to the right side) to conform to a curved bone cavity. For example, the anchor assembly 50 can be inserted into a curved bone cavity in a relaxed or flexible state, when a tensile forced is applied, the anchor segments 52, 54, 56, 58 can be tilted as illustrated herein to form a curved anchoring structure while assuming the substantially rigid configuration inside the bone cavity. In some embodiments, tilting of the anchor segments and/or curving of the anchor assembly can be accomplished by forming an internal cannulation that is not co-axial to the longitudinal axis of the anchor segments. For example, individual anchor segments of the anchor assembly 50 can have lumens that are not co-axial to the longitudinal axis of the segments. As such, when the anchor segments are engaged to adjacent segments in the rigid configuration, the off-axis lumens can form an off-axis internal cannulation where a flexible member (e.g., suture) can exert a tensile force onto the anchor assembly 50, where the tensile force will curve the anchor assembly 50 to an off-axis direction (e.g., right side) as shown.

Figure 6:
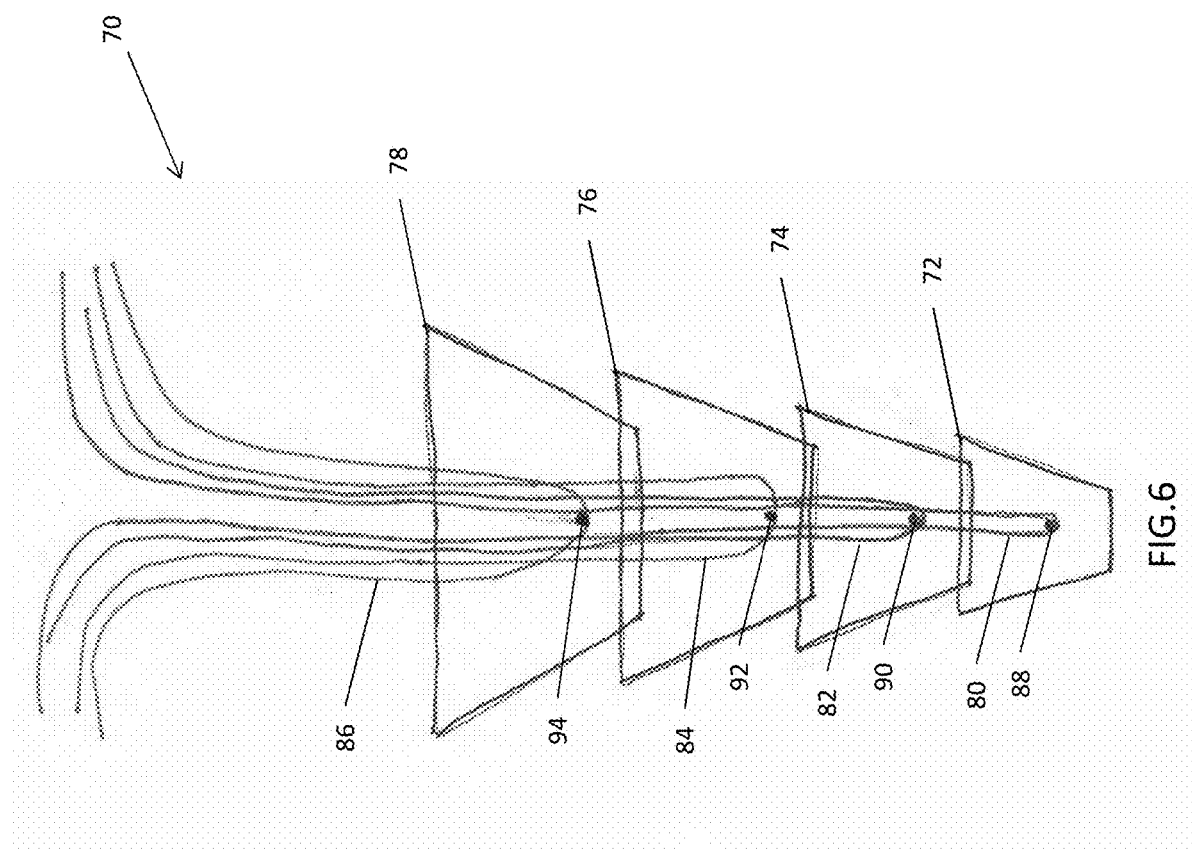
FIG. 6 is a schematic illustration of an anchor assembly with variable sized anchor segments in accordance with some embodiments.

In general, anchor assemblies as described in FIGS. 1-5 have anchor segments that are of substantially the same size and shape. However, in some embodiments, an anchor assembly 70 can include anchor segments 72, 74, 76, 78 that are of different sizes and/or shapes. Such a design can also be configured to increase the anchor assembly's 70 engagement force within a bone cavity. As illustrated in an exemplary embodiment in FIG. 6, the anchor assembly 70 can have anchor segments 72, 74, 76, 78 that are of different sizes such that segment dimensions (e.g., diameter) decrease from a proximal end to a distal end of the assembly 70, with a most distal segment 72 being smallest in size and a proximal segment 78 being the largest. As such, when the anchor assembly 70 is in the rigid configuration, the assembly's overall profile becomes larger due to the larger size of the proximal most segment. Moreover, more than one suture 80, 82, 84, 86 can be inserted through the larger segments for applying additional tensile forces. For example, as illustrated in FIG. 6, in addition to the most distal segment 72 having a suture 80 wrapped across a distal bar 88, a second segment 74 stacked on top of the most distal segment 72 can also have a distal bar 90 and a second suture 82 placed across that distal bar 90. Similarly, a third 76 and fourth 78 anchor segment in the anchor assembly 70 can each have a distal bar 92, 94 and sutures 84, 86 positioned across the bars 92, 94. This configuration 70 advantageously allows a surgeon to apply additional forces to the anchor segments 72, 74, 76, 78 and also allocate forces as appropriate to optimize the engagement force between the anchor assembly 70 and the walls of a bone cavity. It should be noted that different segment and suture combinations can be conveniently utilized in this exemplary embodiment for the purpose of optimizing the engagement force.

Figure 7:
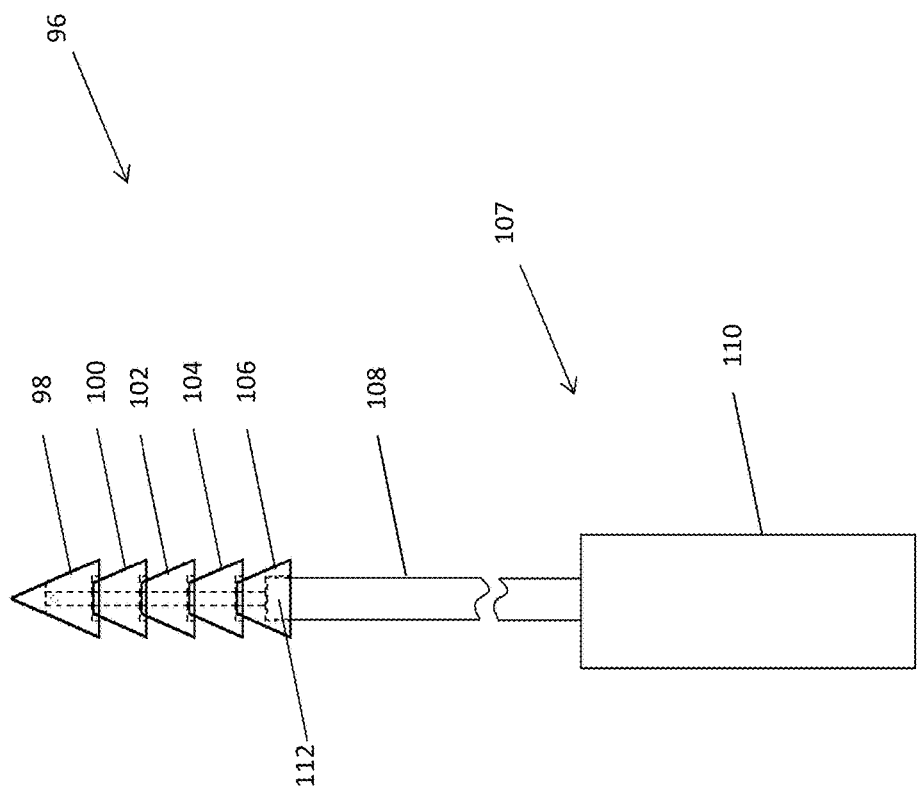
FIG. 7 is a schematic illustration of an anchor assembly coupled to a flexible inserter in accordance with some embodiments.

The anchor assemblies described herein can be used with a variety of inserter tools, which are well known to those skilled in the art. FIG. 7 illustrates anchor assembly 96 attached an inserter tool 107. As illustrated, the inserter tool 107 has a proximal handle 110 with a shaft 108 that extends distally therefrom. The distal end of the shaft can be removably attached to the proximal end of the anchor assembly 96. A person skilled in the art will appreciate that the inserter tool, particularly shaft 108, can be configured as a rigid member, a flexible member, or a malleable member. It will be understood that a variety of mating mechanisms can be used to connect shaft 108 to anchor assembly 96. For example, a proximal anchor segment 106 of the anchor assembly 96 can have an interface element 112 designed to receive the distal end of shaft 108, which can be configured in the manner of a driver to push and/or rotate an anchor into a bone cavity. As explained above, a suture (not shown in FIG. 7) can link together all the anchor segments 98, 100, 102, 104, 106 through an internal cannulation and be attached to the handle 110 in a variety of ways.

The anchor segments disclosed herein can be made from a variety of biologically compatible materials of the type commonly known and used in the manufacture of suture anchors, which may be bioabsorbable or non-bioabsorbable. Suitable materials, by way of non-limiting example, include metals, such as surgical grade titanium, and polymers, such as poly-ether-ether-ketone (PEEK), polylactic acid, polyglycolic acid, and combinations thereof. Other suitable materials include, by way of non-limiting example, a composite of tricalcium phosphate and poly(lactic-co-glycolic acid), such as Biocryl Rapide™ available from DePuy Mitek, Inc. It is possible that different portions of the suture anchor 96 can also be formed from different materials to form the various anchor segments of different materials to provide distinct advantages tailored to each segment.

The dimensions of the anchor segment can vary depending on the intended application, and the overall anchor assembly dimensions will be a function of the number of anchor segments used and the size of the individual anchor segments. By way of example, the length of the individual anchor segments can be in the range of about 0.5 mm to 5 mm, and typically about 1.5 mm. The diameter of the individual anchor segments at the widest portion of the anchor segment can be in the range of about 1 mm to 10 mm, and typically about 3 mm. In embodiments where the anchor segments have a tapering diameter, such as frustrum-shaped or conical anchors, the diameter of the narrower portion of the anchor segment can be in the range of about 0.5 mm to 9.5 mm, and typically about 2.5 mm. A person skilled in the art can determine the suitable segment dimensions, depending on the desired use of the anchor assembly.

The flexible member, such as a suture, to be used with the anchor assemblies described herein can be of a type and possess dimensions so as to allow sufficient working material for a surgeon, for example by being pliable and long enough to connect the segments of the anchor assembly and connect to the handle. The suture can thus be of any length suitable for the various purposes described herein, for example in the range of about 35 cm to 137 cm, and more particularly about 86 cm. The suture can also be of any thickness suitable for the various purposes described herein, for example in the range of about #5-0 to #5 as defined by the United States Pharmocopeia ("USP") size designation. More particularly, the suture can have a thickness of about #2 USP size designation. The suture can be formed of any known suture material, including resorbable, non-resorbable, and/or combinations thereof. Exemplary suture materials include catgut, polyglycolide, and polydioxanone, such as EthiBond® available from Ethicon, Inc. and ORTHOCORD® High Strength Orthopaedic Suture available from DePuy Mitek, Inc. Moreover, the suture can be a monofilament, braided, or woven.

In use and following accepted surgical procedures, involving either open or minimally invasive surgery, an opening or cavity in a bone can be formed prior to delivering a suture anchor assembly. For example, and with reference to FIGS. 8A-9D, a practitioner can use an awl, drill, and/or an inflatable balloon to create an opening 124 in bone 118 that is sufficiently sized to accept the anchor assembly 96.

After formation of the opening in the bone, the suture anchor assembly can be delivered into the opening. In use, the suture anchor assembly is maintained in a delivery configuration while being delivered into the opening, as described above. Once the anchor assembly is properly positioned in the hole 124, the flexible member (i.e., suture 92) is tensioned so as to convert the anchor assembly to a rigid construct.

Figure 8C:
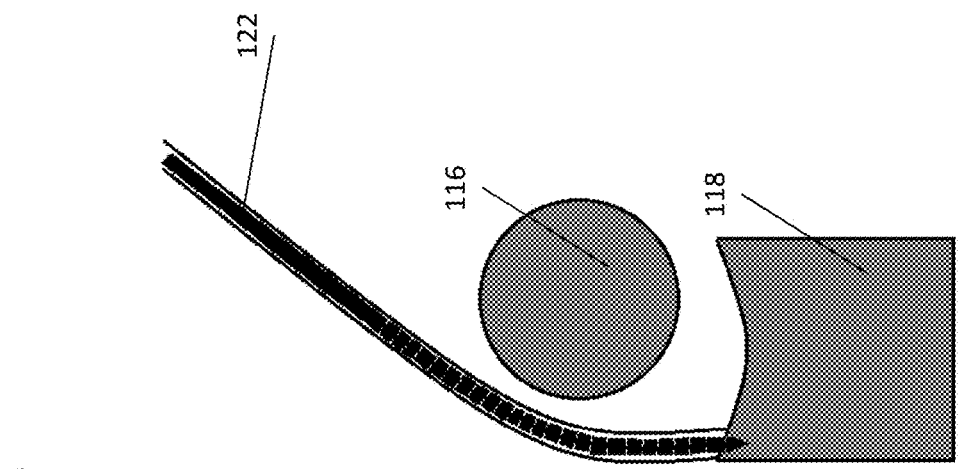
FIG. 8A to 8C are schematic illustrations of steps of forming a bone cavity in accordance with some embodiments.
Figure 8B:
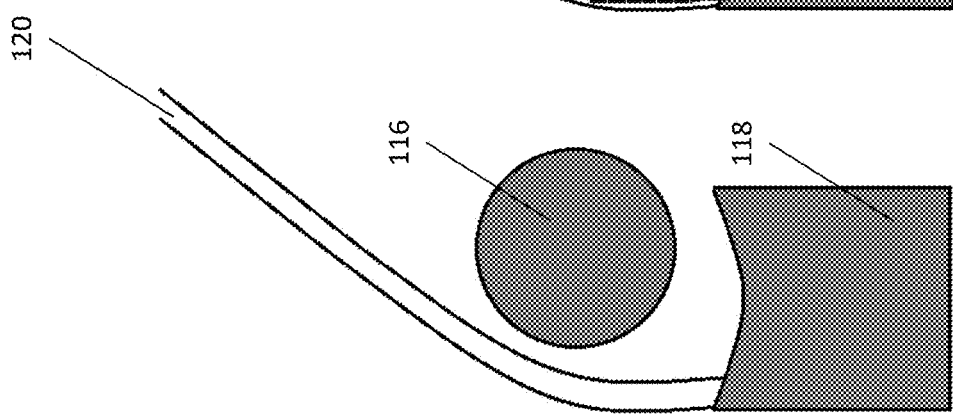
Figure 8A:
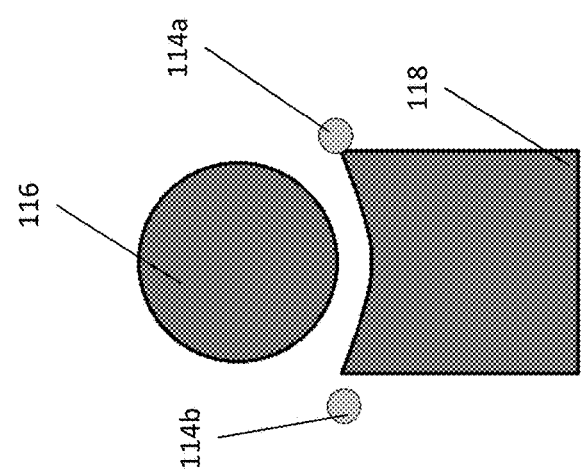

FIGS. 8A-9D illustrate the use of the suture anchor assembly described herein with reference to a surgical procedure to repair a soft tissue tear. For example, when a labrum 114b is detached from a ball 116 and socket 118 joint as shown in FIG. 8A, the anchor assembly 96 can be used to reattach the labrum 114b to the socket bone 118 to a pre-detachment position (see labrum 114a). A drill 122, such as a bendable drill, can be introduced through a drill guide 120 and form a bone cavity 124 by drilling a hole in the socket bone 118 as illustrated in FIGS. 8B and 8C. Once the bone cavity 124 is formed, the anchor assembly 96 can be delivered to the cavity in the delivery configuration in which it is flexible and able to traverse a curved pathway using a flexible inserter 108, as illustrated in FIGS. 9A and 9B. The conical shaped distal segment 98 can facilitate a push-in type insertion of the anchor assembly 96 into the cavity 124, or in some embodiments, threads (not shown) can be incorporated into the segments 98, 100 102, 104, 106 to facilitate a twist-in type insertion. Once the anchor assembly 96 has been fully seated inside the bone cavity 124 as illustrated in FIG. 9C, the suture 92 can be passed through the labrum tissue 114b and the suture 92 can be manipulated to approximate the labrum 114b to the socket bone 118. When the suture 92 is tensioned by a surgeon, the force will cause the anchor assembly 96 to transform into a rigid configuration where the anchor segments are approximated to one another and substantially immovable with respect to one another, thus forming a rigid construct, similar to the rigid configuration illustrated in FIG. 2. The forces that result from placement of the anchor assembly within the cavity 124 and the tensioning of the suture 92 to place the anchor assembly in the rigid configuration will enable the interdigitation features on the anchor segments to create an engagement force sufficient to secure the anchor assembly 96 in place against the walls of cavity 124. Utilizing the anchor assembly 96 as an anchor, the suture 92 is coupled back onto the anchor assembly 96, securing the labrum 114b in a reattached position comparable to the position of a healthy labrum 114a, as illustrated in FIG. 9D.

A person skilled in the art will appreciate that the present disclosure can have application in any application requiring the fixation of any type of soft tissue to bone.

The suture anchor assemblies and inserter tools described herein can be included in surgical kits. For example, a surgical kit for repairing tendon or ligament can include a suture anchor assembly such as that depicted and described herein. That is, the suture anchor assembly can include the appropriate number of anchor segments connected by a suture material. The kit may include a number of different anchor assemblies, each of different sizes and with varying numbers of anchor segments. The surgical kit can further include an inserter tool such as that described with respect to FIG. 7. The inserter tool can be configured to selectively maintain the suture anchor assembly in the delivery configuration until deployment. Further, the surgical kit can have an inserter tool with a suture anchor assembly preloaded into the inserter tool. The surgical kit can include additional items, such as a plurality of suture anchor assemblies, additional suture lengths, tissue preparation tools such as a beath pin, and any other element that is typically used in suture anchor applications.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical fastening device, comprising:
   an anchor assembly formed of a plurality of rigid anchor segments, each including a longitudinal axis, a proximal segment and a distal anchor segment comprising a force transferring element, and at least one segment having at least one interdigitation element configured to create an engagement force between the at least one segment and a tissue; and
   a flexible member linking the plurality of anchor segments and configured to transition the anchor assembly from a first, flexible configuration when the flexible member is in a relaxed state to a second, substantially rigid configuration when the flexible member is in a taut state, wherein the flexible member is a suture configured to connect each of the plurality of anchor segments, and the suture includes a first limb and a second limb, and at least one limb is placed external to a portion of at least one of the plurality of anchor segments, wherein, in the substantially rigid configuration, the longitudinal axis of one of the plurality of anchor segments is non-aligned with the longitudinal axis of an adjacent anchor segment.

2. The device of claim 1, wherein the flexible member is operably coupled to the force transferring element such that the application of a tensile force to the flexible member is effective to compress adjacent segments.

3. The device of claim 1, wherein the distal segment is smaller in diameter than the proximal segment and comprises a substantially conical tip configured to assist an insertion of the plurality of anchor segments into the tissue.

4. The device of claim 1, wherein the force transferring element comprises one of an eyelet, a knot, and a cross pin.

5. The device of claim 1, wherein each anchor segment comprises a receiver element configured to receive the flexible member.

6. The device of claim 5, wherein the receiver element comprises a lumen.

7. The device of claim 6, wherein the lumen extends through each segment such that the lumens of adjacent segments are oriented with respect to each other in one of a coaxial manner and a non-coaxial manner.

8. The device of claim 1, wherein each anchor segment is of a substantially frustrum-like shape.

9. The device of claim 1, wherein a proximal end of the proximal segment includes an interface element configured to receive an inserter tool.

10. The device of claim 1, wherein adjacent ends of adjacent segments are configured to mate to one another.

11. The device of claim 10, wherein the adjacent ends of adjacent segments mate as a ball and socket.

12. The device of claim 1, wherein the interdigitation element comprises a bone engaging surface feature.

13. The device of claim 1, wherein the assembly includes from about 4 to 7 segments.

14. The device of claim 13, wherein the anchor assembly decrease in diameter from the proximal segment to the distal segment.

15. A surgical suture anchor assembly, comprising:
    a plurality of anchor segments configured to selectively interlock with each other, each segment including a receiver element configured to accept a flexible member, a longitudinal axis, a distal end and a proximal end;
    a flexible member extending through the receiver element of each of the plurality of anchor segments, the flexible member being operatively coupled to a force transferring element on a terminal segment and being configured to transform the plurality of anchor segments from a flexible assembly to a substantially rigid body when tension is applied thereto, wherein the flexible member is a suture configured to connect each of the plurality of anchor segments, and the suture includes a first limb and a second limb, and at least one limb is placed external to at least a portion of one of the plurality of anchor segments so that the substantially rigid body includes non-aligned anchor segments when tension is applied, and wherein, in the substantially rigid body, the longitudinal axis of one anchor segment is non-aligned with the longitudinal axis of the adjacent anchor segment.

16. The anchor assembly of claim 15, wherein the receiver element is at least one of a lumen and a slot.

17. The anchor assembly of claim 15, wherein the at least one limb is placed external to at least two nonadjacent anchor segments.

18. A surgical method, comprising:
    delivering a suture anchor assembly formed of a plurality of substantially rigid segments, each segment comprising a longitudinal axis, to a cavity formed in a bone, the suture anchor assembly having a delivery configuration in which the suture anchor assembly is flexible and able to assume a non-linear orientation;
    anchoring the suture anchor assembly in a delivered configuration within the cavity such that the suture anchor assembly assumes a substantially rigid configuration by tensioning a flexible member extending through the assembly, wherein the flexible member is a suture configured to connect each of the plurality of segments, and the suture includes a first limb and a second limb, and at least one limb is placed external to at least one of the plurality of segments so that the substantially rigid configuration includes non-aligned segments, wherein, in the substantially rigid configuration, the longitudinal axis of one segment is non-aligned with the longitudinal axis of the adjacent segment;
    passing a suture attached to the suture anchor assembly through a detached soft tissue; and tensioning the suture to re-approximate detached soft tissue.

19. The method of claim 18, wherein the suture anchor assembly is passed through a curved pathway.

20. The method of claim 18, wherein the at least one limb is placed external to at least two nonadjacent segments.

* * * * *